(12) United States Patent
Steier

(10) Patent No.: US 9,404,817 B2
(45) Date of Patent: Aug. 2, 2016

(54) FILM-TYPE PRESSURE SENSOR E.G. FOR ARTICLE OF FOOTWEAR

(75) Inventor: Andreas Steier, Pellingen (DE)

(73) Assignee: IEE International Electronics & Engineering S.A., Echternach (LU)

(*) Notice: Subject to any disclaimer, the term of this patent is extended or adjusted under 35 U.S.C. 154(b) by 0 days.

(21) Appl. No.: 14/128,728

(22) PCT Filed: Jun. 14, 2012

(86) PCT No.: PCT/EP2012/061362
§ 371 (c)(1),
(2), (4) Date: Dec. 23, 2013

(87) PCT Pub. No.: WO2013/000728
PCT Pub. Date: Jan. 3, 2013

(65) Prior Publication Data
US 2014/0144251 A1    May 29, 2014

(30) Foreign Application Priority Data
Jun. 30, 2011   (LU) .......................................... 91833

(51) Int. Cl.
*G01L 1/20*       (2006.01)
*A43B 3/00*       (2006.01)
*A61B 5/103*      (2006.01)
(Continued)

(52) U.S. Cl.
CPC .............. *G01L 1/205* (2013.01); *A43B 3/0005* (2013.01); *A43B 3/0015* (2013.01); *A43D 1/027* (2013.01); *A61B 5/1038* (2013.01); *A61B 5/6807* (2013.01); *G06F 3/0334* (2013.01); *A61B 2562/0247* (2013.01); *A61B 2562/08* (2013.01)

(58) Field of Classification Search
CPC ............................. G01L 1/205; A43B 3/0005
See application file for complete search history.

(56) References Cited

U.S. PATENT DOCUMENTS 4,745,930 A * 5/1988 Confer .......................... 600/592
5,678,544 A   10/1997 DeLonzor et al.
(Continued)

FOREIGN PATENT DOCUMENTS

CN          101918804 A    12/2010
WO       2009093727 A1     7/2009

OTHER PUBLICATIONS

International Search Report for corresponding application PCT/EP2012/061362 filed Jun. 14, 2012; Mail date Oct. 1, 2012.
(Continued)

*Primary Examiner* — Lisa Caputo
*Assistant Examiner* — Tran M Tran
(74) *Attorney, Agent, or Firm* — Reising Ethington P.C.

(57) ABSTRACT

A film-type pressure sensor includes a carrier structure including a first carrier film, a second carrier film and a spacer film arranged between the first and second carrier films, where one or more pressure-sensing cells are disposed in the carrier structure, each of which includes an electrode arrangement for producing an impedance change in response to a compressive force, an electrical interface is provided for mechanically and electrically connecting the pressure sensor to an evaluation circuit, where some terminals of the interface are connected with the electrode arrangements of the cells so as to allow them to be read out, such that one or more electrical components interconnect at least two of the terminals in pairs so as to form a combination of terminal pair impedances that represents coded information relating to the pressure sensor.

13 Claims, 3 Drawing Sheets

(51) Int. Cl.
*G06F 3/033* (2013.01)
*A43D 1/02* (2006.01)
*A61B 5/00* (2006.01)

(56) References Cited

U.S. PATENT DOCUMENTS

| | | | |
|---|---|---|---|
| 7,453,268 B2 * | 11/2008 | Lin | 324/608 |
| 8,676,541 B2 * | 3/2014 | Schrock et al. | 702/188 |
| 2004/0059197 A1 | 3/2004 | Yamashita et al. | |
| 2007/0056385 A1 | 3/2007 | Lorenz | |
| 2008/0278336 A1 | 11/2008 | Ortega et al. | |
| 2010/0063779 A1 | 3/2010 | Schrock et al. | |

OTHER PUBLICATIONS

Written Opinion for corresponding application PCT/EP2012/061362 filed Jun. 14, 2012; Mail date Oct. 1, 2012.
Chinese Office Action; Chinese Application No. 201280041565.3; Filing Date: Jun. 14, 2012; Date of Mailing: May 13, 2015; 16 pages.
Chinese Office Action; Chinese Application No. 201280041565.3; Filing Date: Jun. 14, 2012; Date of Mailing: Nov. 9, 2015; 5 pages.

* cited by examiner

FILM-TYPE PRESSURE SENSOR E.G. FOR ARTICLE OF FOOTWEAR

TECHNICAL FIELD

The present invention generally relates to film-type pressure sensors. A preferred aspect of the invention related to film-type pressure sensors configured for being integrated into the sole structure of an article of footwear, such as, e.g., a shoe, a boot, a sandal or the like.

BACKGROUND

Film-type pressure sensors are used in a wide range of applications, e.g. as input devices for human-machine or human-computer interaction, or for vehicle seat occupancy sensing and/or classification, and the like.

Document U.S. 2010/0063779 discloses a shoe with an integrated film-type pressure sensor. The sensor system collects performance data that are transferred for further use via a communication port. The shoe contains a force sensor arranged in the sole structure for measuring, in a plurality of areas, pressure (force) exerted by the wearer's foot on the sole structure, and an electronic module configured to gather data from the sensors. The module is configured for transmitting the data to an external device for further processing. In one of the embodiments disclosed in U.S. 2010/0063779, the pressure sensor comprises four elongated pressure-sensing cells, each of which contains a first and a second electrode as well as a force-sensitive resistive material disposed between the electrodes to electrically connect the electrodes together. When pressure is applied to the force-sensitive material, the resistivity of the latter changes and the resulting change in resistance is detected by the electronic module.

In most of today's applications, each pressure sensor comprises its dedicated electronic control module that evaluates the pressure exerted on the one or more pressure-sensing cells. This will not necessarily be the case in the future. Indeed, U.S. 2010/0063779 already mentions that the electronic control module may be removable from the article of footwear at the option of the user. The user may replace it with another, possibly differently configured, module. It is also possible that the user possesses only one pair of electronic control modules, which he uses with different pairs of shoes. Of course, such interchangeability requires some standardization effort. For instance, the electrical interfaces of different film-type pressure sensors have to be compatible with different electronic control modules. However, the different film-type pressure sensors will not be equal in all respects. There could be differences as regards the number, the shape, the position etc. of the pressure-sensing cells, the materials used (and thus the response characteristics) etc. In order for the electronic control module to take such differences into account, the user may thus be required to adjust some settings of the electronic control module when uses it with another pressure sensor. That complicates the exchange procedure and is a potential source of avoidable handling errors.

BRIEF SUMMARY

The invention improves the user-friendliness of film-type pressure sensors.

A film-type pressure sensor includes a carrier structure comprising a first carrier film, a second carrier film and a spacer film arranged between the first and second carrier films. One or more pressure-sensing cells are disposed in the carrier structure, in which the spacer has an opening allowing flexure of the first and/or the second carrier film toward each other under a compressive force, and in which an electrode arrangement is disposed for producing an impedance change in response to the compressive force. The pressure sensor includes an electrical interface for mechanically and electrically connecting the film-type pressure sensor to an evaluation circuit. Some terminals of the electrical interface are electrically connected with the electrode arrangements of the pressure-sensing cells so as to allow them to be read out when the evaluation circuit is connected to the film-type pressure sensor. According to the invention, one or more electrical components (such as, for instance, resistors and/or conductors and/or diodes etc.) interconnect at least two of the terminals in pairs so as to form a combination of terminal pair impedances that represents coded information relating to the film-type pressure sensor. When the evaluation circuit is connected to the film-type pressure sensor, it may detect the combination of terminal pair impedances and look up the encoded information.

As those skilled will appreciate, the coded information is preferably usable by the evaluation circuit to automatically make the settings necessary for properly controlling the film-type pressure sensor. The coded information serves as a "fingerprint" of the pressure sensor that may readily be identified by the evaluation circuit. The user will not be required to manually configure the evaluation circuit.

Preferably, the one or more electrical components are embedded in-between the first and second carrier films.

According to an advantageous embodiment of the invention, the one or more electrical components are printed and/or laminated on the first and/or the second carrier film.

The one or more electrical components preferably comprise at least one of resistors and conductors. Other possibilities would be diodes or capacitors. Combinations of different types of electrical components may be used on one pressure sensor to increase the number of combinations for a given number of terminals.

According to a preferred embodiment of the invention, the electrical interface comprises a common terminal connected to the electrode arrangements of all of the one or more pressure-sensing cells and one or more cell-specific terminals connected to the electrode arrangement of one of the one or more pressure-sensing cells, such that impedance changes produced by the electrode arrangements appear between the common terminal and the cell-specific terminals. With such a configuration, the pressures acting on the one or more pressure-sensing cells may be detected individually. Other circuit configurations are possible: for instance, pressure-sensing cells could be connected in series or in parallel. Thanks to the information coded on the pressure sensor, the evaluation circuit may be enabled to configure itself in accordance with the sensor type connected to it. The electrical interface preferably comprises at least one additional terminal that is interconnected with one or more of the cell-specific terminals, in accordance with the "fingerprint" to be made available for the evaluation circuit.

The evaluation circuit, e.g. a microprocessor, an integrated application-specific circuit, a field-programmable gate array or the like, may be a removable part of the pressure sensor. Preferably, the evaluation circuit is configured to measure the impedances of the electrode arrangements of the pressure-sensing cells and the terminal pair impedances. The evaluation circuit may implement other functionalities, e.g. analysis of the readings, storage of raw or processed data, data transfer via cable or wireless interface to another entity, for instance a personal computer, a mobile phone, a tablet computer, a digital audio player, a heart rate monitor, a wristwatch, a game controller, etc.

According to a preferred aspect of the invention, the film-type pressure sensor and a compatible evaluation device comprising an evaluation circuit connectable to the electrical interface are provided as a kit, the assembly of which may be left to the user.

According to another or complementary aspect of the invention, the pressure sensor is arranged in the sole structure of an article of footwear. Preferably, the article of footwear comprises a receptacle (possibly integrated into the pressure sensor) for an evaluation device with an evaluation circuit connectable to the electrical interface. According to this aspect of the invention, the coded information preferably includes at least one of a shoe size, an indication of whether the article of footwear is for a left or a right foot, a shoe model, a shoe brand, a pressure-sensor model, a production date, a serial number.

It is worthwhile noting that an article of footwear (or a pair thereof) and an evaluation device comprising an evaluation circuit connectable to the electrical interface (or a pair thereof) may be provided as a kit or separately.

The evaluation circuit preferably has implemented therein a library (e.g. in form of a lookup table) allowing decoding of the coded information, i.e. determining which one among a plurality of pre-programmed configurations is to be selected for controlling the pressure sensor connected.

BRIEF DESCRIPTION OF THE DRAWINGS

A preferred embodiment of the invention will now be described, by way of example, with reference to the accompanying drawings in which.

DETAILED DESCRIPTION

Figure 1:
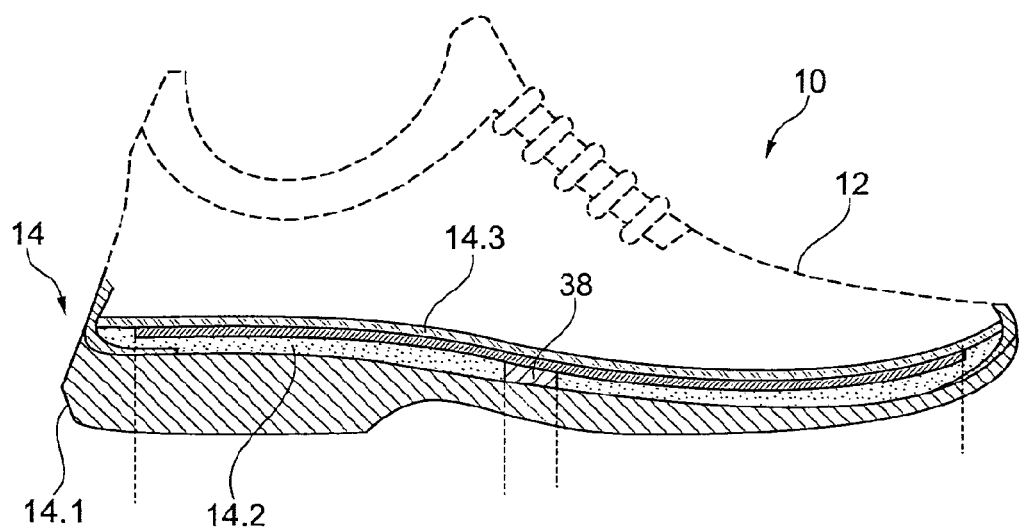
FIG. 1 is a longitudinal cross sectional view of the sole structure of a sports shoe with a film-type pressure sensor.

An article of footwear, in form of a sports shoe 10 is depicted in FIG. 1 as including an upper 12 and a sole structure 14. The upper 12 is secured to sole structure 14 and defines a chamber for receiving a foot. The sole structure 14 includes an outsole 14.1, a midsole 14.2, and an insole 14.3, which forms the bottom of the foot-receiving chamber of the sport shoe 10. The midsole 14.2, which is preferably formed of impact-attenuating material, has a film-type pressure sensor 16 attached to its upper surface. When the insole is in place, the pressure sensor 10 is thus sandwiched between the insole 14.3 and the midsole 14.2.

Figure 2:
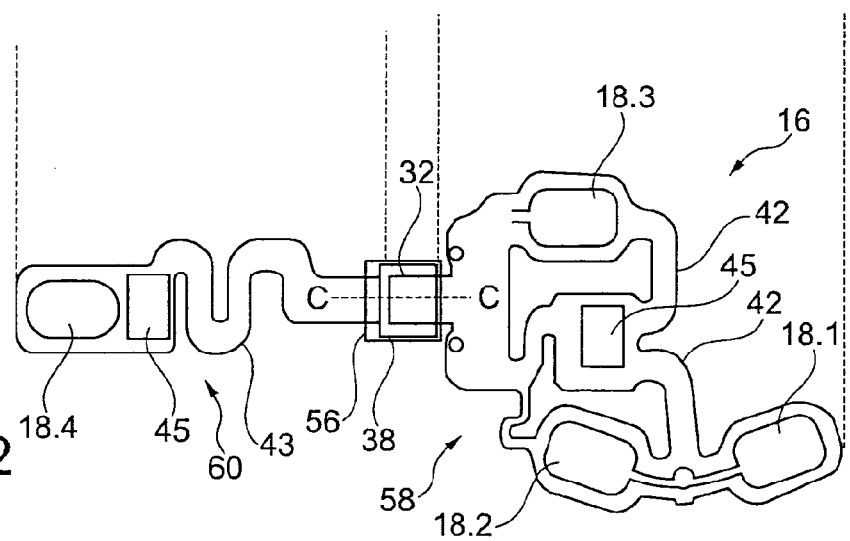
FIG. 2 is a top view of the pressure sensor of the sports shoe of FIG. 1.

As best shown in FIG. 2, the pressure sensor 16 comprises a plurality of pressure-sensing cells 18.1, 18.2, 18.3, 18.4, commonly referred to by reference number 18, located in different areas of the sole structure 14, for measuring pressure exerted by the wearer's foot on the sole structure 14.

Figure 3:
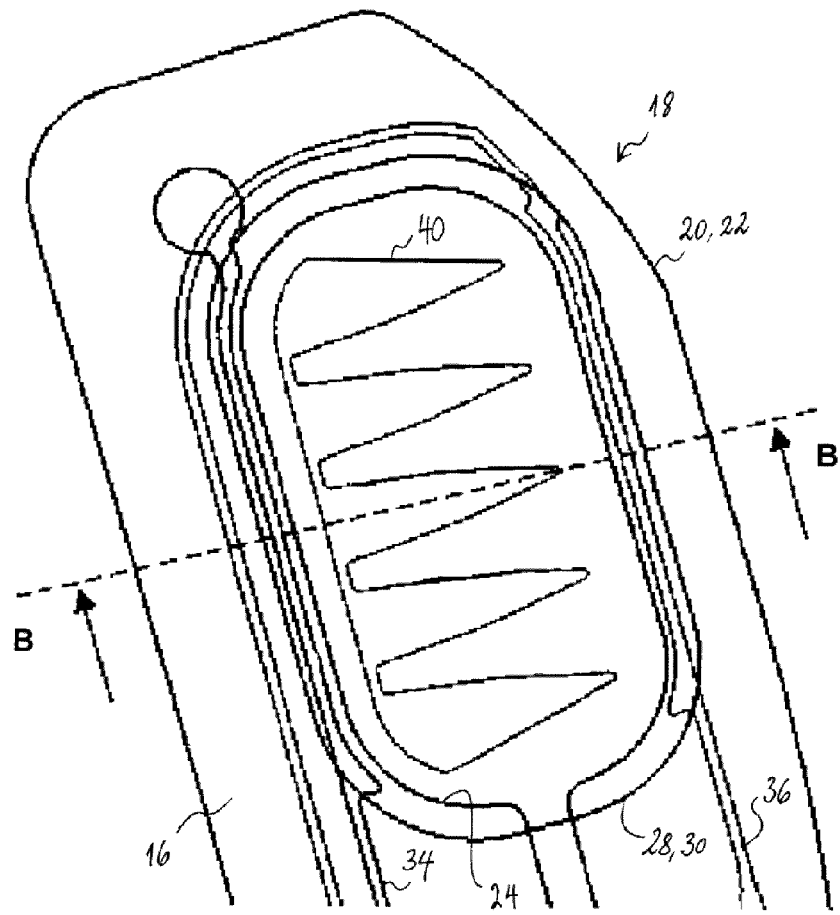
FIG. 3 is a top schematic view of one of the pressure sensing cells of the pressure sensor of FIG. 2.
Figure 4:
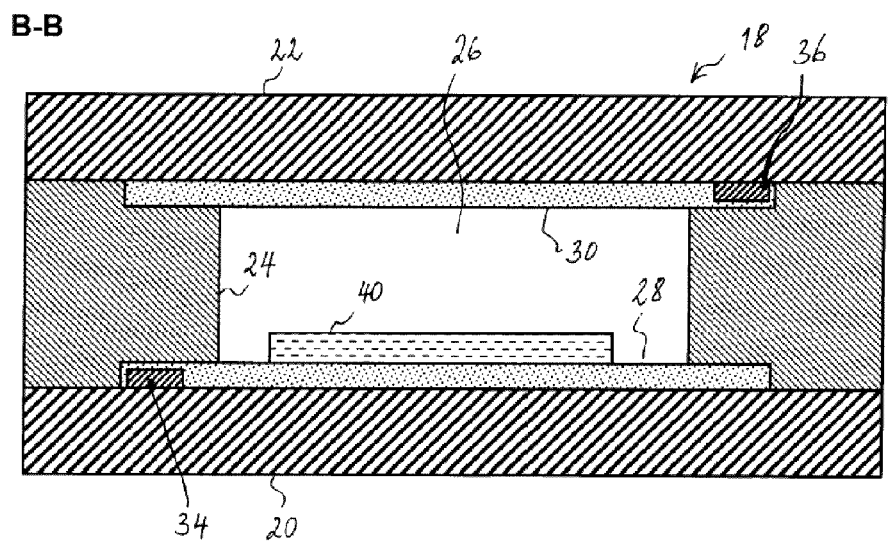
FIG. 4 is a schematic cross sectional view of the B-B plane of FIG. 3.

The configuration of the pressure sensor 16 and its pressure sensing cells 18 will now be described with reference to FIGS. 3 and 4. FIG. 3 shows the contours of the elements of a pressure-sensing cell 18. The pressure sensor 16 comprises a multilayered carrier structure including a first carrier film 20, a second carrier film 22, and a spacer 24. The spacer 24 is typically a double-sided adhesive, with which the first and second carrier films 20, 22 are laminated together. The first and second carrier films 20, 22 are preferably made of PET but other materials such as PEN, PI, PEEK etc. are also possible. Each of the carrier films 20, 22 may consist of a single film layer or comprise a plurality of film layers of the same or different materials. The spacer 24 preferably comprises a PET, PEN, PI, PEEK, etc. film layer with an adhesive coating applied on each side thereof. At each pressure-sensing cell 18, the spacer comprises an opening 26, within which the first and second carrier films 20, 22 may be pressed together. In each pressure-sensing cell 18, a first resistive electrode 28 is permanently arranged on the first carrier film 20 and a second resistive electrode 30 is permanently arranged on the second carrier film 22, in facing relationship with the first electrode 28. Each electrode 28, 30 is contacted by a respective strip conductor 34, 36, which runs alongside the long sides of the opening 26 and which connects the electrode arrangement of each pressure-sensing cell with terminals of an electrical interface portion 32 (see FIG. 2) provided for mechanically and electrically connecting the pressure sensor 16 to an electronic control module 38 (see FIG. 2) that comprises an evaluation circuit for measuring the variable impedance of the pressure-sensing cells 18 and thus the pressure exerted thereon.

In response to pressure acting on the pressure-sensing cell, at least one of the first and second carrier films 20, 22, deflects towards the other carrier film until the carrier films 20, 22 or the elements on their respective inner surface come into contact. Once contact is established, the radius of the mechanical contact surface increases with increasing pressure. When a direct contact is established between the electrodes 28 and 30, the electrical resistance between the conductors 34 and 36 becomes finite and a current may flow in consequence. In this example, electrode 28 is partially covered with an electrically insulating layer 40 (e.g. a dielectric layer) in order to tailor the electrical response of the pressure-sensing cell. As the contact area between the first and second electrodes 28, 30 increases, the resistance measurable between the conductors 34 and 36 decreases. The positions of the contacts between the resistive electrodes 28, 30 and the respective strip conductor 34, 36, the specific resistance of the resistive electrodes, and the shape of the electrically insulating layer 40 determine the pressure-dependent cell resistance.

For fixation of the pressure sensor 16 to the sole structure 14, the pressure sensor 16 comprises one or more fixation pads 45 (see FIG. 2). The fixation pads 45 preferably comprise a layer of pressure-sensitive or heat-activatable adhesive, initially protected by a release liner, which is removed just before the pressure sensor 16 is attached to its carrier member of the sole structure 14.

The electronic control module 38 is removably attached to the multilayer film structure of the pressure-sensor 10 at the interface portion 32. Connection strips 42 interconnect the pressure sensing cells 18 and the interface portion 32. The interface portion 32 and the connection strips 42 are integral part of the multilayer film structure of the pressure sensor 16 and carry the conductive tracks (strip conductors 34, 36) that electrically connect the first and second electrodes 28, 30 of each pressure-sensing cell 18 with a terminal on the interface portion 32. One or more of the connection strips 42 may have a serpentine shape to act as springs and to thereby increase the pressure-sensor's elasticity in the sensor plane.

The electronic control module 38 preferably comprises an application-specific integrated circuit (ASIC), a field-programmable gate array (FPGA), a microprocessor, or the like. Advantageously, the electronic control module 38 is configured for wirelessly transmitting the collected pressure data or any data derived therefrom to a receiver appliance having a user interface. Such receiver appliance could include a (wrist-) watch, the wrist receiver of a heart rate monitor, a handheld computer, a mobile phone, a portable media player or the like. In the illustrated embodiment, the electronic control module 38 is arranged in a cavity or well of the midsole 14.2. The cavity or well may be located elsewhere in the sole structure 14 in other embodiments.

Possible configurations of the flexible circuits of the pressure sensor 16 will now be discussed with reference to FIGS. 5 and 6, which show corresponding schematic block diagrams. In these figures, the pressure-sensing cells 18.1-18.4 are drawn as variable resistors. Conductors arranged on the first carrier film 20 (i.e. between the first carrier film 20 and the spacer 24) are drawn as continuous lines, whereas conductors arranged on the second carrier film 22 (i.e. between the second carrier film 22 and the spacer 24) are drawn as dotted lines. Each one of the pressure-sensing cells 18.1-18.4 is connected between a respective cell-specific terminal 44.1-44.4 and a common terminal 46. The terminals are all arranged in the interface portion 32 (FIG. 2) of the pressure sensor 16 in such a way that they are in contact with corresponding terminals of the electronic control module 38 (FIG. 2). When the electronic control module 38 is connected to the interface portion, it determines the pressures exerted on the pressure-sensing cells 18.1-18.4 based upon the resistance (or the current or the voltage if one of these quantities is kept constant) between each terminal 44.1, 44.2, 44.3 or 44.4 and the common terminal 46. In the illustrated examples, the pressure-sensing cells are through-mode cells, i.e. the electrodes that are in contact with the conductors 34, 36 leading to each cell are arranged on the first and the second carrier film, respectively. In order to avoid that terminals have to be provided on both carrier films, the second strip conductor is routed to the first carrier film using a through-connection 37 across the spacer 24.

Some of the cell-specific terminals 44.1-44.4 are interconnected with an additional terminal 48 by electrical components. That interconnection pattern serves as a "fingerprint" readable by the electronic control module 38 (when it is connected). To read the "fingerprint", the electronic control module detects the impedances between the additional terminal 48 and each one of the cell-specific terminals 44.1-44.4. The fingerprint advantageously represents information relating to the type of pressure-sensor that allows the electronic control module to automatically adjust internal parameters concerning the manner the film-type pressure sensor has to be read out. For instance, the assignment of the terminals could be different from one type of pressure-sensor to another. The control module could look up such information based upon the "fingerprint".

Figure 5:
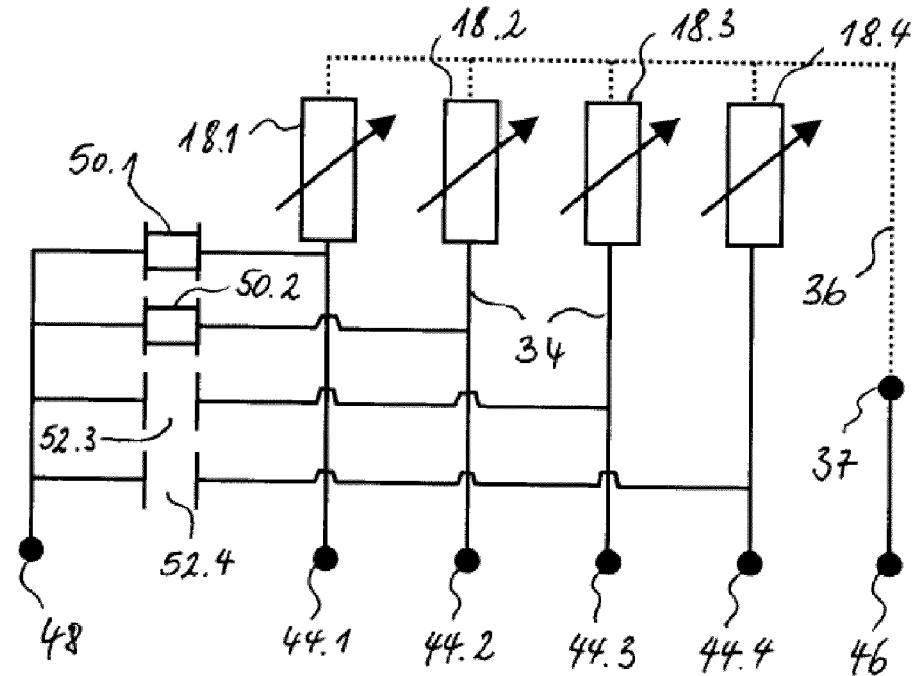
FIG. 5 is a block diagram of the electrical circuit of the pressure sensor illustrated in FIG. 2.

Turning to FIG. 5, the additional terminal 48 and each of the cell-specific terminals are either interconnected by a resistor (e.g. resistor 50.1 between terminals 48 and 44.1 or resistor 50.2 between terminals 48 and 44.2) or not connected (circuit break 52.3 between terminals 48 and 44.3 or circuit break 52.4 between terminals 48 and 44.4). For each pair of terminals, there are two possibilities (circuit break or resistive connection). Accordingly, the number of different configurations in this example amounts to $2^4$=16. However, one advantageously requires that there is at least one resistive connection in order to be able to exclude an accidental circuit beak e.g. at the additional terminal 48.

It should be noted that the cell response curve is influenced by changes in resistivity of the electrode material, which may vary depending on ageing, temperature, humidity or other environmental influences. To be able to correct or compensate such influence on the pressure values, one or more of the resistors 50.1 or 50.2 may serve as reference resistors. In this case, the resistor 50.1 and/or 50.2 is made of the same material as the electrodes 28, 30. It is arranged somewhere on the pressure sensor 16 so that it experiences essentially the same environmental influences as the electrodes 28, 30. If a reference resistor is necessary, this is of course another reason to require that at least one resistive connection be provided between the additional terminal 48 and the cell-specific terminals 44.1-44.4. Alternatively, a separate reference resistor may be provided.

In the example shown in FIG. 5, the resistors 50.1 and 50.2 are resistive prints (sandwiched e.g. between the first carrier film 20 and the spacer film 24) that are connected at both ends by conductors leading to the corresponding terminals. Another possibility would be to arrange the resistors as preloaded pressure-sensing cells (i.e. a pressure-sensing cells wherein the electrodes are permanently kept in contact).

Figure 6:
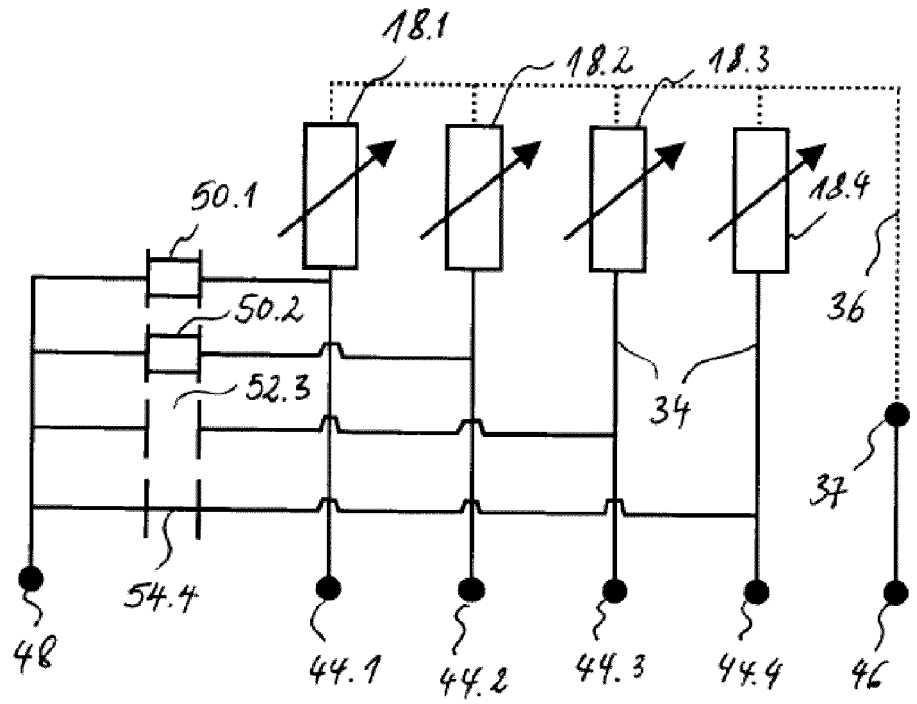
FIG. 6 is a schematic block diagram of an alternative electrical circuit for the pressure sensor of FIG. 2.

In the example of FIG. 6, there are three possibilities for interconnecting the additional terminal 48 and the cell-specific terminals 44.1-44.4:

Resistive interconnection (in FIG. 6 by resistors 50.1, 50.2),
Circuit break (in FIG. 6 between terminals 48 and 44.3) and
Conductive interconnection (in FIG. 6 by short 54.4 between terminals 48 and 44.4).

Those skilled will appreciate that this increases the number of available fingerprints. In the configuration of FIG. 6, it should however be avoided to provide more than one shunt at a time, since otherwise there would be a short-circuit between two or more of the cell-specific terminals, making it impossible to individually detect the pressures exerted on the corresponding cells.

To further increase the number of terminal pair impedance combinations, further terminals may be provided. Alternatively or additionally, resistors with different resistance may be used. Although it is not shown in the drawings, one could also interconnect combinations of the cell-specific terminals 44.1-44.4 and the common terminal 46.

Figure 7:
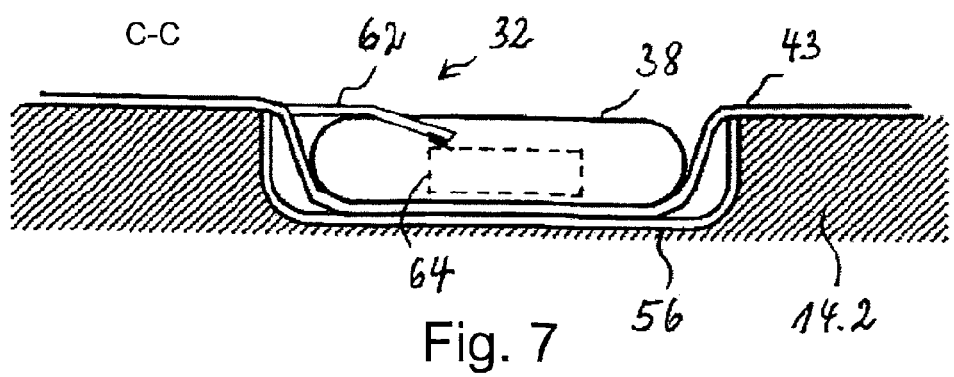
FIG. 7 is a schematic cross sectional view of the C-C plane of FIG. 2.

Turning again to the example of the article of footwear, it will be appreciated that the electronic control module 38 is removably arranged in a receptacle 56 (see FIGS. 2 and 7). FIG. 7 shows the longitudinal cross section C-C of FIG. 2. The connection strip 43 that connects the forefoot portion 58 and the heel portion 60 of the film-type pressure sensor 16 is guided though the trough-shaped receptacle 56 for the electronic control module 38. The receptacle 56 is preferably made of a plastic material (e.g. PET or epoxy). The wall thickness of the receptacle 56 is such that it can withstand the stresses in the middle area of the shoe without substantial deformation and/or breaking. The connection strip 43 is firmly bonded to the bottom of the receptacle 56, so that it is the receptacle 56 that takes up most of the strains occurring in this area during rolling off of the foot and so that the connection strip 43 is prevented from ejecting the electronic control module 38 out of the receptacle 56 when tension is applied to it.

In the area of the connection strip 43, the upper (second) carrier film of the pressure sensor is interrupted and detached from the spacer film 24 and the first carrier film in such a way that a tongue or flap 62 is formed. This tongue or flap 62 forms the electrical interface 32 for the electronic control module 38 and it carries the terminals (see FIGS. 5 and 6), which are removably connected to the evaluation circuit 64 of the electronic control module 46. In the connection strip 43, the strip conductors are all routed between the bottom (first) carrier film and the spacer film. Accordingly, feedthrough contacts are arranged to lead those strip conductors that are normally sandwiched between the second carrier film and the spacer to the first carrier film. Similar feedthrough contacts are provided to lead those strip conductors that are normally sandwiched between the first carrier film and the spacer to the tongue or flap 62.

While a specific embodiment has been described in detail, those with ordinary skill in the art will appreciate that various modifications and alternatives to those details could be developed in light of the overall teachings of the disclosure. Accordingly, the particular arrangements disclosed are meant to be illustrative only and not limiting as to the scope of the invention, which is to be given the full breadth of the appended claims and any and all equivalents thereof.

In particular, the invention has been illustrated by means of the example of a shoe equipped with a film-type pressure sensor. Nevertheless, it will be appreciated that the usability of film-type pressure sensors according to the invention is not limited to the field of footwear. Film-type pressure sensors according to the invention may indeed be used in a number of other applications, e.g. in input devices for human-machine or human-computer interaction, in occupancy sensors for the automotive or other industries, etc.

Furthermore, in the example described in detail, the pressure-sensing cells are configured as so-called through-mode pressure-sensing cells. Those skilled will understand that the pressure-sensing cells could also be configured as so-called shunt-mode pressure-sensing cells, wherein a first and a third electrodes are in contact with the conductors leading to each cell and are arranged on the same carrier film. The second electrode is in this case a shunt element, which is brought into contact with the first and the third electrode when pressure is applied. The electrically insulating layer in this case locally prevents a direct contact between the first and the second electrode, and possibly also between the third and the second electrode.

The invention claimed is:

1. Film-type pressure sensor comprising:
   a carrier structure comprising a first carrier film, a second carrier film and a spacer film arranged between said first and second carrier films,
   one or more pressure-sensing cells disposed in said carrier structure, in which said spacer has an opening allowing flexure of said first and/or said second carrier film toward each other under a compressive force, and in which an electrode arrangement is disposed for producing an impedance change in response to said compressive force; and
   an electrical interface for mechanically and electrically connecting said film-type pressure sensor to an evaluation circuit, said electrical interface comprising a plurality of cell-specific terminals, at least some of which are electrically connected to said the electrode arrangements of said pressure-sensing cells so as to allow them to be read out when said evaluation circuit is connected to said film-type pressure sensor;
   wherein said film-type pressure sensor comprises one or more electrical components that forms an interconnection pattern between one of the said plurality of cell-specific terminals and another additional terminal so as to form a combination of terminal pair impedances,
   wherein said evaluation circuit detects said combination of terminal pair impedances that represents uniquely coded identifying information, that would identify a particular type of said film-type pressure sensor, when said evaluation circuit is connected to said film-type pressure sensor, and
   wherein the coded identifying information is readable by said evaluation circuit before triggering said film-type pressure sensor.

2. Film-type pressure sensor as claimed in claim 1, wherein said one or more electrical components are embedded in-between said first and second carrier films.

3. Film-type pressure sensor as claimed in claim 1, wherein said one or more electrical components are printed and/or laminated on said first and/or said second carrier film.

4. Film-type pressure sensor as claimed in claim 1, wherein said one or more electrical components comprise at least one of resistors and conductors.

5. Film-type pressure sensor as claimed in claim 1, wherein said electrical interface comprises a common terminal connected to the electrode arrangements of all of said one or more pressure-sensing cells and one or more cell-specific terminals connected to the electrode arrangement of one of said one or more pressure-sensing cells, such that impedance changes produced by said electrode arrangements appear between said common terminal and said cell-specific terminals.

6. Film-type pressure sensor as claimed in claim 5, wherein said electrical interface comprises at least one additional terminal, and wherein said one or more electrical components interconnect said at least one additional terminal with one or more of said cell-specific terminals.

7. Film-type pressure sensor as claimed in claim 1, wherein said evaluation circuit is connected to said electrical interface, said evaluation circuit being configured to measure impedances of the electrode arrangements of said pressure-sensing cells and said terminal pair impedances.

8. Film-type pressure sensor as claimed in claim 7, said evaluation circuit having implemented therein a library allowing decoding of said coded identifying information.

9. Film-type pressure sensor as claimed in claim 8, wherein said evaluation circuit is configured to carry out self-adjustments depending on said coded identifying information.

10. Kit, comprising said film-type pressure sensor as claimed in claim 1, and an evaluation device comprising the evaluation circuit connectable to said electrical interface, said evaluation circuit being configured to measure impedances of the electrode arrangements of said pressure-sensing cells and said terminal pair impedances.

11. Kit as claimed in claim 10, said evaluation circuit having implemented therein a library allowing decoding of said coded identifying information.

12. Kit as claimed in claim 10, wherein said evaluation circuit is configured to carry out self-adjustments depending on said coded identifying information.

13. The film-type pressure sensor of claim 1, wherein the coded identifying information generated according to the terminal pair impedances identifies the film-type pressure sensor as a particular type of film-type pressure sensor among a plurality of different types of film-type pressure sensors compatible with the evaluation circuit.

* * * * *